United States Patent [19]

Santangelo

[11] Patent Number: 5,534,004
[45] Date of Patent: Jul. 9, 1996

[54] DEVICE FOR PREVENTIVE SUPPORT OF THE FEMUR

[76] Inventor: Massimo Santangelo, Via Collegio di Spagna, 23, 40054 Bologna, Italy

[21] Appl. No.: 271,024

[22] Filed: Jul. 6, 1994

[30] Foreign Application Priority Data

Jul. 23, 1993 [EP] European Pat. Off. ............. 93830328

[51] Int. Cl.⁶ .................................................. A61B 17/78
[52] U.S. Cl. ................................................ 606/68; 606/66
[58] Field of Search .................................. 606/62, 63, 66, 606/67, 68, 60, 72, 232

[56] References Cited

U.S. PATENT DOCUMENTS

| | | | |
|---|---|---|---|
| 2,699,774 | 1/1955 | Livingston | 606/68 |
| 4,204,531 | 5/1980 | Aginsky | 606/63 |
| 4,453,539 | 6/1984 | Raftopoulos et al. | 606/63 |
| 4,981,481 | 1/1991 | Kranz et al. | 606/62 |
| 5,057,103 | 10/1991 | Davis | 606/68 |
| 5,084,053 | 1/1992 | Ender | 606/104 |
| 5,116,335 | 5/1992 | Hannon et al. | 606/63 |

FOREIGN PATENT DOCUMENTS 2260839   6/1974   Germany.

*Primary Examiner*—Michael H. Thaler
*Assistant Examiner*—Scott B. Markow
*Attorney, Agent, or Firm*—Fay, Sharpe, Beall, Fagan, Minnich & McKee

[57] ABSTRACT

Hip joints are reinforced preventively by a device composed of a tubular element fashioned from biocompatible material, accommodated by a socket drilled in the femoral bone parallel and adjacent to an axis connecting the ball and the diaphysis, and two independent locking assemblies operating unidirectionally and in mutual opposition, likewise of biocompatible material, by which the tubular element can be deformed and manipulated in such a manner as to lodge stably in the surrounding bone tissue of the socket, establishing a load-bearing axis that functions as a bridge between the weaker axis and the main axis of the femur.

5 Claims, 2 Drawing Sheets

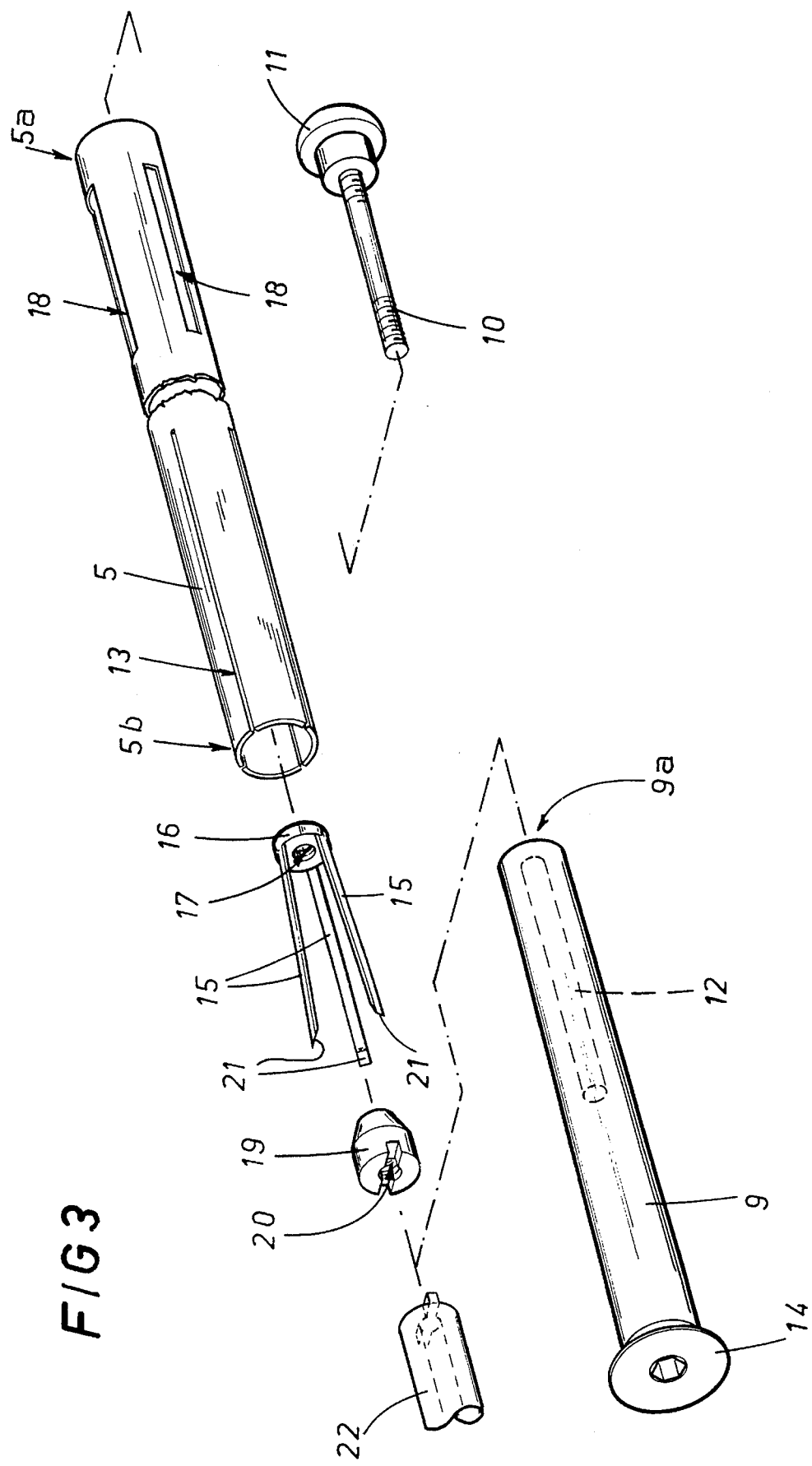

DEVICE FOR PREVENTIVE SUPPORT OF THE FEMUR

BACKGROUND Of the INVENTION

The present invention relates to a device for the preventive support of femoral regions. It has been observed in the medical world, and in particular the orthopedic branch of medicine, that the number of hospitalization cases involving bone fractures has risen considerably over recent years, with a large proportion of such fractures affecting the hip region.

One reason for a greater abundance of fractures is to be found in the increasing growth of the elderly population, and therefore in a higher incidence of osteoporosis, i.e. the process, ocurring typically in old age, by which bones become thin and brittle through lack of calcium.

The bone formations tending more than others to be affected by osteoporosis are those characterized by a "cantilever", such as the femur-pelvis structure. More exactly, the proximal extremity of the femur, comprising the ball, the neck and the topmost part of the diaphysis, is required to support the weight of the body, which, bearing down on the ball of the femur, is transmitted to the diaphysis through the lever arm afforded by the narrow neck of the bone. As discernible from FIG. 1 of the drawings attached to the present specification, the group of elements in question broadly resembles an upturned 'L' on which the weight of the body impinges directly from above, in such a manner that the resulting vertical force FV is applied to the projecting end of the horizontal member of the upturned 'L'; accordingly, this same projecting member (the ball TF) tends to bend, or if stressed beyond a certain limit, to fracture at the junction with the vertical member of the 'L' (at the base B of the neck CF). Required as it is to withstand the dynamic stresses generated daily in ambulation, the physiological composition of the femur presents a structure of osseous lamellae arranged in bundles and disposed along lines coinciding with the mechanical forces to be accommodated: a first pair of such bundles (denominated principal and secondary traction) extending from the proximal lateral extremity of the diaphysis substantially up to the extremities of the ball and neck, and a second pair of bundles (denominated principal and secondary compression) extending from the proximal medial extremity of the diaphysis to the uppermost part of the ball and the neck.

Osteoporosis is essentially the process by which the ends of the osseous lamellar structures become thinner to the point ultimately of exposing an area less able to withstand the load normally applied; the area in question, known as Ward's triangle, is located at the base of the neck portion where most femoral fractures typically occur.

With the recent advent of computerized X-ray bone scanning methods, consultants are provided with a swift, secure and precise evaluation of the state of regression of the aforementioned bundles, and therefore with a basis on which to assess the risk of fracture a patient is likely to encounter unless suitable corrective action is taken.

Hitherto, at all events, the problem in question has been addressed by medical/orthopedic research only in terms of post-fracture remedies; in effect, the prior art embraces orthopedic solutions (for example plates and pins) designed and applied so as to allow the rehabilitation of a fractured femur (see also EP 311,556 and EP 425,472) according to the type and localization of the fracture and the age of the patient.

In the light of the foregoing, it may be asserted that there are currently no systems, or at least that there have as yet been no specific solutions or devices researched and developed, designed to prevent a possible fracture of the femur caused by osteoporosis, notwithstanding the availability of methods by which to examine the condition.

Accordingly, the object of the present invention is to provide a device structured in such a way as to afford a preventive means of support applicable to the proximal extremity of the femur, for patients exposed to the risk of fracture due to regression of the osseous lamellar bundles in cases of femoral osteoporosis, such as can be inserted swiftly, in a normal surgery environment, and offer a secure and economically accessible solution for the patient.

SUMMARY OF THE INVENTION

The stated object is fully realized, according to the present invention, in a device functioning as a preventive hip reinforcement designed for insertion into the proximal extremity of the femur, the part of the femoral bone in question being composed of a ball, and a neck portion extending laterally from the ball along a first axis angled in relation to a rectilinear second axis substantially coinciding with that of the femoral diaphysis, to which the neck portion is attached.

Such a device comprises a tubular element fashioned in biocompatible material, stably insertable into a blind socket drilled in the femoral bone parallel with and adjacent to the first axis, also first and second locking means likewise of a biocompatible material, operating unidirectionally and in mutual opposition in such a way as to determine a partial variation in the external shape of the tubular element, the effect of which being to secure the tubular element stably against the bone surface of the socket and thus establish a load-bearing axis to bridge the first axis and the second axis.

BRIEF DESCRIPTION of the DRAWINGS

The invention will now be described in detail, by way of example, with the aid of the accompanying drawings, in which:

FIG. 3 is an exploded illustration of the device according to the present invention;

DESCRIPTION OF THE PREFERRED EMBODIMENTS

Figure 2:
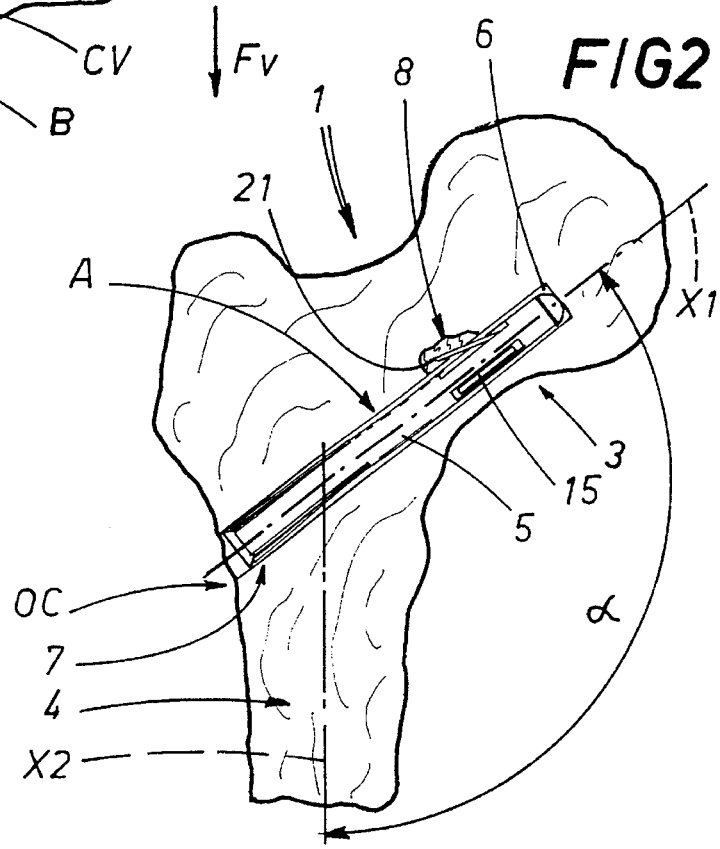
FIG. 2 shows the device according to the invention in side elevation and partly in section, inserted into the proximal extremity of a femur as in FIG. 1.

With reference initially to FIG. 2 of the drawings, 1 denotes a femur of which the proximal extremity consists essentially in a ball 2, united to a neck portion 3 extending along a first axis denoted X1; this first axis is disposed at a substantially obtuse angle $\alpha$ in relation to a rectilinear second axis denoted X2, constituting the longitudinal axis of the femoral diaphysis 4 to which the neck 3 is attached.

Figure 4:
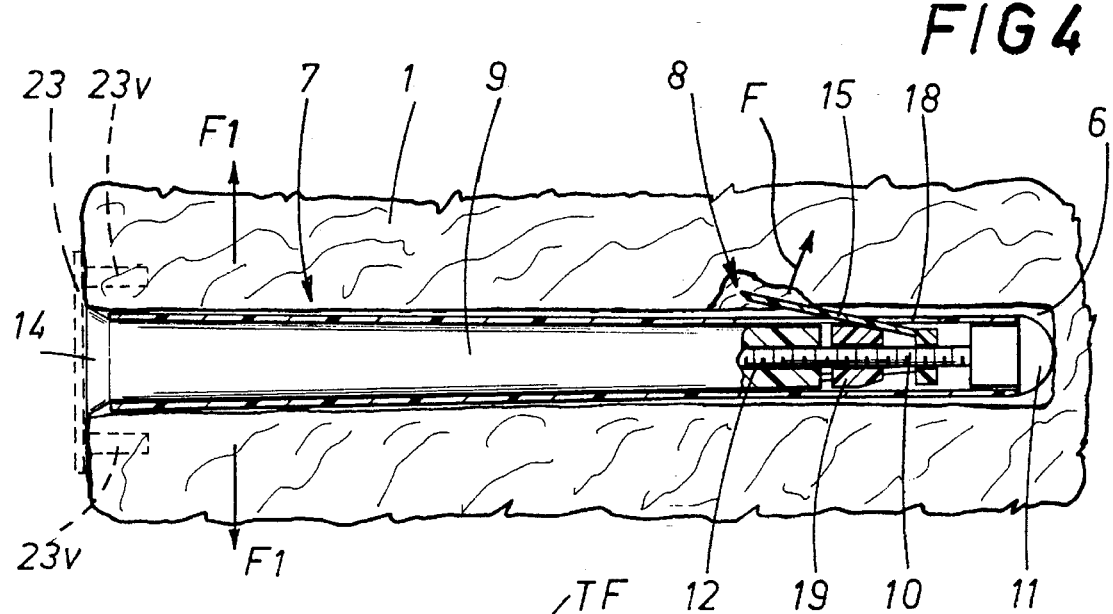
FIG. 4 illustrates the device of FIG. 2 in a side elevation with certain parts in section, seen fully assembled and occupying a corresponding socket in the bone.
Figure 1:
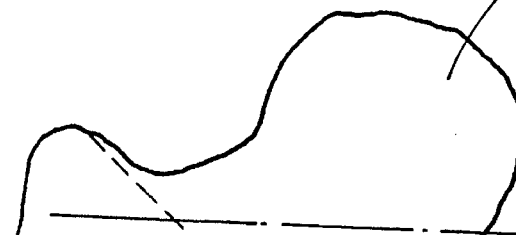
FIG. 1 illustrates the proximal extremity of a femur, viewed in a schematic side elevation and showing lines of force impinging on the parts of the relative bone structure.

Referring also to FIG. 3 and FIG. 4, a preventive support device for application to the extremity of a femoral bone as described above is composed of the following essential component parts: a tubular element 5, also first and second locking means 7 and 8, functioning unidirectionally and in mutual opposition, by which the tubular element is secured internally of a blind socket 6 formed in a part of the neck portion 3. Such first and second locking means 7 and 8 are designed to operate by inducing a partial deformation of the tubular element 5, which is thus made to lodge stably in the socket 6. More exactly, the tubular element 5 is embodied as a hollow cylinder fashioned from a biocompatible material and affording two open ends 5a and 5b, of which one (that denoted 5b) exhibits a plurality of longitudinal cuts 13 spaced apart one from another at identical distance around the circumference of the cylinder, whilst the remaining end 5a affords three longitudinally disposed slots 18, likewise distributed uniformly around the circumference of the tubular element 5; the function of the cuts 13 and slots 18 will be described more fully in due course.

The first undirectional locking means 7 consist in a tapered expansion pin 9 insertable coaxially into the tubular element 5, which is interposed between the innermost end 5a of the hollow cylinder and the second locking means 8. The tapered expansion pin 9 is invested with movement internally of the tubular element 5 by interacting with threaded means 10 in the form of a screw occupying the innermost end 5a of the cylinder. The screw 10 is rigidly associated with a domed cap 11 enclosing the respective open end 5a and disposed in opposition to the innermost end 9a of the tapered pin 9, which in turn affords a threaded hole 12 to accommodate the screw 10. The end of the tapered pin 9 remote from the end 9a affording the threaded hole 12 remains positioned externally of the tubular element 5, and affords a shoulder or stop 14 destined to locate against the corresponding end 5a of the hollow cylinder. The second unidirectional locking means 8 might be embodied to advantage as a set of three deformable prongs 15, each of which permanently anchored at one end to a ring 16 insertable into the tubular element 5 and affording a threaded central hole 17 matched to the thread of the screw 10. The single prongs 15 are provided with a sharp edge 21 at the unattached end, and deformable by spreading apart in such a way as to project through and beyond the three slots 18 afforded by the tubular element 5. Deformation of the prongs 15 is brought about by a circular expansion cone 19 interposed between the prongs and the corresponding innermost end 9a of the tapered pin 9. The cone 19 likewise affords a central threaded hole 20 matched to the thread of the screw 10, and is rotatable by means of a hollow driver 22 in such a way that its forward movement along the screw forces the prongs 15 apart.

In practical application, the device disclosed will be implanted in a patient diagnosed as affected by a strong regression of the osseous lamellar bundles of the proximal femoral extremity; the procedure is as follows.

With the assistance of X-ray equipment and using a guide wire, the surgeon proceeds to position a drilling tool at the point selected for insertion of the device, substantially on the lateral side of the femoral diaphysis 4. The tool, a hollow borer, is of a conventional type utilized in orthopedic surgery (and therefore not illustrated). The femur can then be drilled in a direction parallel to the axis X1 of the neck portion 3 (see FIG. 2), in such a way as form the socket The tool is withdrawn subsequently to allow the introduction of the tubular element 5, which will be preassembled with the prongs 15 and expansion cone 19 both inserted and retained by the screw 10 together with the cap 11. Having seated the device initially in the socket, the surgeon proceeds to advance the cone 19 along the screw 10 by means of the driver 22, with the result that the prongs 15 are forced out through the slots 18 (see arrow F, FIG. 4) as a consequence of the thrust generated by combined rotation and translation of the cone; the prongs 15 remain stably in position by virtue of their being anchored to the ring 16, which in turn is coupled to the screw 10. As the sharp edges 21 of the prongs 15 penetrate the surrounding bone tissue, the tubular element 5 is locked in place and disallowed any rotational movement about its own longitudinal axis. With the prongs 15 securely seated, the tapered pin 9 can be inserted into the tubular element 5.

The pin 9, which is first coupled to the end of the screw 10 remote from the cap 11, and then rotated from externally by the surgeon using a conventional Allen type key, advances forcibly into the tubular element 5 in such a manner as to deform and expand the end 5a incorporating the cuts 13 (see arrow F1, FIG. 4), to the point at which the external surface of the element 5 enters into firm contact with the wall of the socket 6. To obtain a secure locking action, at all events, the surgeon can continue rotating until the shoulder 14 of the pin 9 is in abutment with the end 5b of the tubular element 5. In this situation, the device is restrained stably by the socket 6 both axially (through the action of the tapered pin 9) and in the angular direction (by the prongs 15), in such a way as to create a load bearing axis A bridging the two main axes X1 and X2 of the bone structure.

The support obtained in this manner affords notable security inasmuch as the lateral end of the tubular element 5 lodges in the osseous cortex, denoted OC in FIG. 2, which is extremely tough, and unaffected by osteoporosis.

In the event that the locking action might not be considered altogether satisfactory, the lateral end of the device can be capped by means of a special plate 23, illustrated with phantom lines in FIG. 4, which is fashioned in biocompatible material and fastened to the osseous cortex OC with relative screws 23v, thereby rendering the installation of the device totally secure.

The device according to the invention thus provides a patient affected by osteoporosis with a means of support that is swift, safe and inexpensive to fit. To reiterate, the function of the device disclosed is essentially one of establishing a load-bearing axis precisely across the part of the femur most likely to fracture (the base of the neck portion), by replacing those lamellar bundles which have become thin and already weakened to the point that the patient is no longer able to enjoy complete ambulatory function or sustain a normal level of physical effort.

The device is also easily implanted in a surgery environment, using local anaesthetic, and therefore immensely advantageous in terms of cost and time both for the orthopedist and for the patient, who is rendered able almost immediately (effectively, in a few minutes) to resume walking normally and without difficulty or discomfort.

What is claimed:

1. A device for preventive support of a proximal extremity of a femoral bone consisting of a ball associated with a neck portion extending along a first axis disposed at an angle relative to a rectilinear second axis substantially coinciding with a femoral diaphysis to which the neck portion is attached, the device comprising:

a tubular element having first and second ends fashioned from biocompatible material, and stably insertable into a blind socket created in the femoral bone parallel with and in a region of the first axis;

first and second locking means fashioned from biocompatible material, the first locking means designed to effect a partial variation in an external shape of the tubular element and said second locking means connected to the tubular element for expanding to engage the femoral bone, the first and second locking means thereby securing the tubular element stably against a bone surface of the blind socket thereby establishing a load-bearing axis that bridges the first axis and the second axis, the second locking means further including a set of elongated prongs, each prong being integrally connected at one end to a ring inserted into the tubular element, the first locking means further including a rotatable tapered expansion pin, inserted coaxially into the tubular element to assume a position interposed between the first end of the tubular element and the second locking means, the second locking means being positioned internally within the tubular element its ring being connected to a screw which is positioned near the second end of the tubular element, the screw further having a cap which closes an opening in the second end of the tubular element and which secures the screw against axial movement through the tubular element, the tapered pin having a threaded bore for receiving the screw.

2. A device as in claim 1, wherein a wall of the tubular element further includes a plurality of longitudinal cuts near the first end, uniformly distributed around a circumference of the tubular element which allows a portion of the tubular element near the first end to expand as the tapered pin is rotated, the expanded portion secures the tubular element stably against the bone surface by providing axial restraint of the tubular element with respect to the blind socket.

3. A device as in claim 1, wherein the tapered pin further includes first and second ends, the tapered pin first end including a travel limiting shoulder designed to abut with the first end of the tubular element, the tapered pin second end including the threaded bore.

4. A device as in claim 1, wherein the ring further includes a central hole to receive the screw, the second locking means further including a circular expansion cone interposed between the ring and the tapered pin and having a central threaded hole the expansion cone causing the prongs to spread apart forcibly one from another and project through and beyond respective slots contained in a wall of the tubular element as the tapered pin is rotated.

5. A device as in claim 4, wherein the prongs are at least three in number and distributed uniformly around an axis of the tubular element, each prong having a sharp edge at a first end of the prong which is remote from a second end of the prong which is anchored to the ring.

* * * * *